US007951748B2

(12) United States Patent
Lu et al.

(10) Patent No.: US 7,951,748 B2
(45) Date of Patent: May 31, 2011

(54) METHOD OF PREPARING A SHAPED CATALYST, THE CATALYST, AND USE OF THE CATALYST

(75) Inventors: Jian Lu, Houston, TX (US); Theofiel Meuris, Magnolia, TX (US)

(73) Assignee: Shell Oil Company, Houston, TX (US)

( * ) Notice: Subject to any disclaimer, the term of this patent is extended or adjusted under 35 U.S.C. 154(b) by 448 days.

(21) Appl. No.: 11/501,297

(22) Filed: Aug. 9, 2006

(65) Prior Publication Data

US 2007/0100151 A1 May 3, 2007

Related U.S. Application Data

(60) Provisional application No. 60/707,506, filed on Aug. 11, 2005.

(51) Int. Cl.
*B01J 29/04* (2006.01)
*B01J 23/58* (2006.01)
*B01J 23/02* (2006.01)
*C07D 301/10* (2006.01)

(52) U.S. Cl. .......... 502/344; 502/60; 502/330; 502/340; 549/534

(58) Field of Classification Search .................... 502/60, 502/330, 340, 344; 549/534
See application file for complete search history.

(56) References Cited

U.S. PATENT DOCUMENTS

| | | | |
|---|---|---|---|
| 3,819,537 A | 6/1974 | Chan | 252/476 |
| 3,824,196 A | 7/1974 | Benbow et al. | 252/455 |
| 3,856,709 A | 12/1974 | Porta et al. | 252/463 |
| 3,890,104 A | 6/1975 | Porta et al. | 23/288 |
| 3,950,507 A | 4/1976 | Kuklina et al. | 423/626 |
| 3,962,285 A | 6/1976 | Cusumano | 260/345 |
| 4,005,049 A | 1/1977 | Fields | 252/467 |
| 4,039,561 A | 8/1977 | Mitsuhata et al. | 260/348.34 |
| 4,045,369 A | 8/1977 | Cantaluppi | 252/432 |
| 4,299,735 A | 11/1981 | Mein et al. | 252/465 |
| 4,320,031 A | 3/1982 | Parthasarathy et al. | 252/432 |
| 4,379,134 A | 4/1983 | Weber et al. | 423/626 |
| 4,742,034 A | 5/1988 | Boxhoorn et al. | 502/231 |
| 4,761,394 A | 8/1988 | Lauritzen | 502/348 |
| 4,766,105 A | 8/1988 | Lauritzen | 502/216 |
| 4,783,437 A | 11/1988 | Boxhoorn | 502/348 |
| 4,806,518 A | 2/1989 | Boxhoorn et al. | 502/231 |
| 4,822,900 A | 4/1989 | Hayden | 549/534 |
| 4,845,253 A | 7/1989 | Bowman | 549/536 |
| 4,845,296 A | 7/1989 | Ahmed et al. | 564/477 |
| 4,874,739 A | 10/1989 | Boxhoorn | 502/218 |
| 4,994,589 A | 2/1991 | Notermann | 549/534 |
| 5,100,859 A | 3/1992 | Gerdes et al. | 502/439 |
| 5,145,824 A | 9/1992 | Buffum et al. | 502/216 |
| 5,384,302 A | 1/1995 | Gerdes et al. | 502/439 |
| 5,512,530 A | 4/1996 | Gerdes et al. | 502/351 |
| 5,733,842 A | 3/1998 | Gerdes et al. | 502/439 |
| 5,864,047 A | 1/1999 | Gaffney | 549/536 |
| 5,935,898 A * | 8/1999 | Trubenbach et al. | 502/300 |
| 6,153,556 A | 11/2000 | Shima et al. | 502/348 |
| 6,281,370 B1 | 8/2001 | Shima et al. | 549/534 |
| 6,313,325 B1 | 11/2001 | Shima et al. | 549/534 |
| 6,368,998 B1 | 4/2002 | Lockemeyer | 502/347 |
| 2002/0103390 A1 | 8/2002 | Shima et al. | 549/523 |
| 2004/0110973 A1 | 6/2004 | Matusz | 549/534 |
| 2006/0036104 A1 | 2/2006 | Lu et al. | 549/512 |
| 2006/0036105 A1 | 2/2006 | Lu et al. | 549/512 |

FOREIGN PATENT DOCUMENTS

| | | |
|---|---|---|
| CA | 1282772 | 4/1991 |
| EP | 3642 | 8/1979 |
| EP | 3642 | 7/1984 |
| EP | 425020 | 5/1991 |
| GB | 798234 | 7/1958 |
| WO | 2004/030813 | 4/2004 |
| WO | WO2004030813 | 4/2004 |
| WO | 2004/039496 | 5/2004 |
| WO | WO2004039496 | 5/2004 |
| WO | WO2006020718 | 2/2006 |

OTHER PUBLICATIONS

Brunnauer, S., Emmett, P. Y. and Teller, E., Journal of American Chem. Soc., 60, pp. 309-316 (1938).
"Encyclopedia of Catalysis", I T Horvath (Ed.) 202. pp. 246-264, Sep. 2008.
Kirk-Othmer Encyclopedia of Chemical Technology, 3rd edition, vol. 9, 1980, pp. 445-447.
Size Enlargement by Agglomeration, by Wolfgang Pietsch (John Wiley & Sons, 1991) pp. 12-18 & 118.
Brunauer, S., Emmett, P. Y. and Teller, E., J. Am. Chem. Soc., 60, 309-16 (1938).
International Search Report mailed Feb. 17, 2006 for International application No. PCT/US2005/028437, International filing date Aug. 11, 2005.
Written Opinion of the International Search Authority mailed Feb. 17, 2006 for International application No. PCT/US2005/028437, International filing date Aug. 11, 2005.

* cited by examiner

*Primary Examiner* — Victor Oh

(57) ABSTRACT

A method of preparing a shaped catalyst, which method comprises molding a dough into shaped particles and drying the shaped particles, wherein the dough comprises a support material, or a precursor thereof, and a silver component; the shaped catalyst, and a use of the shaped catalyst.

25 Claims, No Drawings

METHOD OF PREPARING A SHAPED CATALYST, THE CATALYST, AND USE OF THE CATALYST

This application claims the benefit of U.S. Provisional Application No. 60/707,506 filed Aug. 11, 2005 the entire disclosure of which is hereby incorporated by reference.

FIELD OF THE INVENTION

The invention relates to a method of preparing a shaped catalyst, and a shaped catalyst which is obtainable by the method. The invention also relates to a process for the epoxidation of an olefin, which process comprises contacting a feed comprising the olefin and oxygen with the shaped catalyst. The invention also relates to a method of using the olefin oxide so produced for making a 1,2-diol, a 1,2-diol ether or an alkanolamine.

BACKGROUND OF THE INVENTION

In olefin epoxidation an olefin is reacted with oxygen in the presence of a silver-based catalyst to form the olefin epoxide. The olefin oxide may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine.

Conventional silver-based catalysts have provided the olefin oxide notoriously in a low selectivity. For example, when using a conventional catalyst, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation $$7C_2H_4+6O_2=>6C_2H_4O+2CO_2+2H_2O,$$

cf. Kirk-Othmer's *Encyclopedia of Chemical Technology*, 3$^{rd}$ ed., Vol. 9, 1980, p. 445.

The catalysts are also subject to an aging-related performance decline during normal operation. The aging manifests itself by a reduction in the activity of the catalyst. Usually, when a reduction in activity of the catalyst is manifest, the reaction temperature is increased in order to compensate for the reduction in activity. The reaction temperature may be increased until it becomes undesirably high, at which point in time the catalyst is deemed to be at the end of its lifetime and would need to be exchanged.

Generally, the commercially applied olefin epoxidation catalysts are shaped catalysts which comprise silver deposited on a support. They are prepared by a method which involves impregnating or coating the shaped support with a solution comprising a silver component. The support is commonly prepared by moulding a dough comprising the support material or a precursor thereof into shaped particles and drying the particles at a high temperature of, for example, at least 1000° C. Numerous patent publications disclose examples of such catalyst preparation.

Over the years much effort has been devoted to improving olefin epoxidation catalysts in their performance, for example in respect of their initial activity and selectivity, and in respect of their stability performance, that is their resistance against the aging-related performance decline. Solutions have been found in improved compositions of the catalysts, and, in other instances, solutions have been found in improved processes of preparing the catalysts.

Modern silver-based catalysts are more selective towards olefin oxide production. When using the modern catalysts in the epoxidation of ethylene the selectivity towards ethylene oxide can reach values above the 6/7 or 85.7 mole-% limit referred to hereinbefore. Such high-selectivity catalysts may comprise as their active components silver, and one or more high-selectivity dopants, such as components comprising rhenium, tungsten, chromium or molybdenum. High-selectivity catalysts are disclosed, for example, in U.S. Pat. No. 4,761,394 and U.S. Pat. No. 4,766,105.

In respect of improved processes of preparing the catalysts, for example, U.S. Pat. No. 6,153,556 shows that utilizing a support prepared by mixing α-alumina particles with a silicon compound, an organic binder, and a metal or compound selected from the Groups Ib and IIb in the Periodic Table of elements leads to catalysts which have improved initial performance properties.

WO 2004/030813 shows that forming shaped particles from a paste comprising an alkaline earth metal carbonate support material and a silver bonding additive improves the mechanical properties of the resulting support.

In some instances, epoxidation catalysts are formed from a dough comprising silver in addition to the support material. In particular, with respect to such epoxidation catalysts, it may be desirable to improve the attrition resistance of the catalysts. Within commercial processes, friction or rubbing occurs between the catalysts themselves or between the catalyst and equipment surfaces. This friction or rubbing may occur during catalyst manufacturing, catalyst shipping, epoxidation reactor loading, or other reactor processes. These forces can cause the catalyst to breakdown into smaller particles called fines. This physical breakdown of the catalyst is known as attrition.

Attrition occurring during the loading of the catalyst into the epoxidation reactor can cause dusting problems which results in a loss of valuable catalyst. The difficulty associated with attrition with respect to the epoxidation process is that the fines can be driven away from the reaction zone, resulting in 1) excessive developments of the reaction in the separators or other locations within the oxidation process and 2) creating problems in the recovery systems. The loss of catalyst reduces the productivity of the catalyst bed effecting overall process efficiency and increasing operating costs. Thus, it would be highly desirable to improve the attrition resistance of catalysts.

It also goes without saying that—despite the many improvements already seen—it remains highly desirable to improve the performance, in respect of one or more of activity, selectivity and stability, of olefin epoxidation catalysts formed from a dough comprising silver in addition to the support material.

SUMMARY OF THE INVENTION

The invention provides a method of preparing a shaped catalyst, which method comprises moulding a dough into shaped particles and drying the shaped particles, wherein the dough comprises a support material, or a precursor thereof, and a silver component, and wherein the support material, or the precursor thereof, has a $d_{90}$ of at most 12.5 µm and at least 10.5% v and at most 80% v of the support material, or the precursor thereof, has a particle size less than 2 µm.

The invention also provides a shaped catalyst which is obtainable by the method in accordance with this invention.

The invention also provides a process for the epoxidation of an olefin, which process comprises contacting a feed comprising the olefin and oxygen with a shaped catalyst which is obtainable by the method in accordance with this invention.

The invention also provides a method of using an olefin oxide for making a 1,2-diol, a 1,2-diol ether or an alkanolamine comprising converting an olefin oxide into the 1,2-diol, the 1,2-diol ether, or the alkanolamine, wherein the olefin oxide has been obtained by a process for the epoxidation of an olefin in accordance with this invention.

DETAILED DESCRIPTION OF THE INVENTION

Catalysts prepared in accordance with this invention can exhibit unexpectedly an improved attrition resistance and performance in olefin epoxidation.

The improved performance of the catalysts prepared in accordance with this invention is apparent from one or more of an improved initial activity, improved initial selectivity, improved activity stability and improved selectivity stability. Initial selectivity is meant to be the maximum selectivity which is achieved in the initial phase of the use of the catalyst wherein the catalyst slowly but steadily exhibits an increasing selectivity until the selectivity approaches a maximum selectivity, which is termed the initial selectivity. The initial selectivity is usually reached before a cumulative olefin oxide production over the catalyst bed has amounted to, for example, 0.2 kTon/m³ of catalyst bed or 0.15 kTon/m³ of catalyst bed, in particular 0.1 kTon/m³ of catalyst bed. The invention provides as an advantage that less process steps are involved in preparing a shaped catalyst starting from a particulate support material than in the case where a particulate support material is first shaped and the shaped support particles are provided with catalytically active materials.

The support material for use in this invention may be natural or artificial inorganic particulate materials and they may include refractory materials, silicon carbide, clays, zeolites, charcoal and alkaline earth metal carbonates, for example calcium carbonate or magnesium carbonate. Preferred are refractory materials, such as alumina, magnesia, zirconia and silica. The most preferred material is α-alumina. Typically, the support material comprises at least 85% w, more typically 90% w, in particular 95% w α-alumina or a precursor thereof, frequently up to 99.9% w, or even up to 100% w, α-alumina or a precursor thereof. The α-alumina may be obtained by mineralization of α-alumina, suitably by boron or, preferably, fluoride mineralization. Fluoride mineralized α-alumina may be of a platelet structure. A preferred α-alumina is of such platelet structure. Reference is made to U.S. Pat. No. 3,950,507, U.S. Pat. No. 4,379,134 and U.S. Pat. No. 4,994,589, which are incorporated herein by reference.

Precursors of support materials may be chosen from a wide range. For example, α-alumina precursors include hydrated aluminas, such as boehmite, pseudoboehmite, and gibbsite, as well as transition aluminas, such as the chi, kappa, gamma, delta, theta, and eta aluminas.

The particle size distribution of the support material or precursor thereof may be monomodal, or multimodal, for example bimodal or trimodal. The support material or precursor thereof may be formed from a single particulate material or a mixture of two or more particulate materials which yield an overall particle size distribution for the support material. A particulate material contains a plurality of particulates having various particle sizes. Typically, the support material or a precursor thereof has a $d_{50}$ of at least 0.2 μm, more typically at least 0.5 μm, in particular at least 1 μm, more in particular at least 2 μm. Typically, the support material or a precursor thereof has a $d_{50}$ of at most 6.5 μm, more typically at most 6 μm, most typically at most 5.5 μm, in particular at most 5 μm, more in particular at most 4 μm, most in particular at most 3.5 μm.

Typically, the support material or a precursor thereof has a $d_{90}$ of at least 6 μm, more typically at least 9 μm, in particular at least 10 μm, more in particular at least 1 μm. Typically, the support material or a precursor thereof has a $d_{90}$ of at most 14.5 μm, more typically at most 14 μm, in particular at most 13 μm, more in particular at most 12.5 μm, most in particular at most 12 μm.

Typically, the support material or a precursor thereof has a $d_{10}$ of at least 0.1 μm, more typically at least 0.2 μm, in particular at least 0.5 μm, more in particular at least 1 μm. Typically, the support material or a precursor thereof has a $d_{10}$ of at most 3.5 μm, more typically at most 3 μm, in particular at most 2.5 μm, more in particular at most 2 μm.

Typically, from 70 to 100% v, in particular 80 to 100% v, of the support material or precursor thereof has a particle size within the range of from 10 to 1000% of the $d_{50}$ value of the particle size distribution. More typically, from 60 to 100% v, in particular 80 to 100% v, of the support material or a precursor thereof has a particle size within the range of from 20 to 600% of the $d_{50}$ value of the particle size distribution.

In an embodiment, the span of the particle size distribution curve (hereinafter "PSDC") may be characterized by the following equation:

$$\text{PSDC}=(d_{90}-d_{10})/d_{50}$$

The term "particle size", as used herein, is the equivalent diameter of a particle as detected by a Micromeritics Saturn DigiSizer 5200 laser diffraction particle size analyzer. The equivalent diameter is the diameter of a reference sphere having known properties and producing the same response in the sensing instrument as the particle being measured. The term "particle size distribution", as used herein, relates to the volume fraction of the particles for a given particle size as detected by a Micromeritics Saturn DigiSizer 5200 laser diffraction particle size analyzer. The method for measuring particle size includes dispersing the particles by ultrasonic treatment, thus breaking up secondary particles into primary particles. This sonification treatment is continued until no further change in the $d_{50}$ value is noticed, which typically requires 1 minute sonification at 100 Watts and 0.1% Sodium metaphosphate when using the Micromeritics Saturn DigiSizer 5200 laser particle size analyzer.

The term "$d_{50}$", as used herein, represents a particle diameter at which there are equal spherical equivalent volumes of particles larger and particles smaller than the stated median particle size.

The term "$d_{90}$", as used herein, represents a particle diameter where ninety percent by volume of the particles are smaller than the stated value for $d_{90}$.

The term "$d_{10}$" as used herein, represents a particle diameter where ten percent by volume of the particles are smaller than the stated value for $d_{10}$.

Typically, the value for the span of the particle size distribution curve is in the range of from 0.1 to 10, more typically from 0.2 to 8, in particular 0.4 to 6, more in particular 0.5 to 2.5.

In an embodiment, the support material or precursor thereof has a particle size distribution such that at least 0.1% v, typically at least 0.5% v, more typically at least 1% v, in particular at least 5% v, more in particular at least 10% v, and most in particular at least 15% v of the support material or a precursor thereof has a particle size less than 1 μm. Typically, the particle size distribution is such that at most 75% v, typically at most 55% v, in particular at most 45% v of the support material or a precursor thereof has a particle size less than 1 μm.

Typically, at least 10.5% v, more typically at least 11% v, most typically at least 12% v, in particular at least 15% v, more in particular at least 20% v, and most in particular at least 25% v of the support material or a precursor thereof has a particle size less than 2 μm. Typically, the particle size distribution is such that at most 80% v, typically at most 60% v, in particular at most 50% v of the support material or a precursor thereof has a particle size less than 2 μm.

Typically at least 15% v, more typically at least 20% v, in particular at least 25% v, more in particular at least 30% v of the support material or a precursor thereof has a particle size less than 3 μm. Typically, the particle size distribution is such that at most 80% v, typically at most 70% v, in particular at most 60% v of the support material or a precursor thereof has a particle size less than 3 μm.

Typically, the particle size distribution is such that at least 50% v, typically at least 53% v, more typically at least 55% v, in particular at least 60% v of the support material or a precursor thereof has a particle size less than 5 μm. Typically, the particle size distribution is such that at most 95% v, typically at most 90% v, more typically at most 85% v, in particular at most 80% v of the support material or a precursor thereof has a particle size of less than 5 μm.

Typically, the particle size distribution is such that more than 75% v, typically at least 80% v, more typically at least 85% v, in particular at least 90% v of the support material or a precursor thereof has a particle size less than 10 μm. Typically, the particle size distribution is such that at most 99% v, typically at most 95% v, more typically at most 93% v, most typically at most 92% v, in particular at most 91% v, more in particular at most 90% v of the support material or a precursor thereof has a particle size of less than 10 μm.

Typically, the particle size distribution is such that 100% v, of the support material or a precursor thereof has a particle size less than 100 μm, more typically less than 90 μm, in particular less than 80 μm, more in particular less than 75 μm, most in particular less than 50 μm.

In an embodiment, more than 25% v, typically at least 30% v, in particular at least 35% v of the support material or a precursor thereof has a particle size in the range of from 2 to 5 μm.

In an embodiment, at least 3% v, typically at least 4% v, more typically at least 6% v, in particular at least 8% v, and more in particular at least 10% v of the support material or a precursor thereof has a particle size in the range of from 10 to 20 μm.

In an embodiment, the support material or precursor thereof may be a mixture of particulate materials of different particle sizes. In particular, the support material may be a mixture containing (1) one or more finer particulate materials comprising particulates having a $d_{50}$ of at most 3 μm, typically at most 1 μm in a quantity of at least 1% w, typically at least 5% w, and more typically in the range of from 10 to 30% w, relative to the total weight of the support material or precursor thereof; and (2) one or more coarser particulate materials comprising particulates having a $d_{50}$ of more than 3 μm, typically at least 5 μm in a quantity of at most 99% w, typically at most 95% w, and more typically in the range of from 70 to 90% w, relative to the total weight of the support material or precursor thereof.

The effect of having the particle sizes as described above in the support material is an improvement in the attrition resistance and activity of the shaped catalyst. This effect can be achieved independent of whether the shaped particles are dried at a temperature below 1000° C., or at 1000° C. or above.

The support material or precursor thereof may typically have a surface area in the range of from 0.1 to 5 m²/g, more typically from 0.2 to 2 m²/g, in particular from 0.5 to 1.5 m²/g. "Surface area" as used herein is understood to refer to the surface area as determined by the BET (Brunauer, Emmett and Teller) method as described in Journal of the American Chemical Society 60 (1938) pp. 309-316.

A bond material may or may not be incorporated into the dough. The bond material is a material which facilitates bonding the particles of the support material or precursor thereof together. The bond material also may form a coating on at least a part of the support surface, which makes the support surface more receptive.

In particular when the support material is α-alumina, the bond material may typically be based on a silica-containing composition, for example, a silica sol, a precipitated silica, an amorphous silica, or an amorphous alkali metal silicate, alkaline earth metal silicate or aluminosilicate. Typically, the silica-containing compositions for use as a bond material may also comprise hydrated alumina and/or an alkali metal salt, such as a carbonate, bicarbonate, formate, acetate, nitrate, or sulfate. Typically, the alkali metal is lithium, sodium, or potassium, or a combination thereof.

In advantageous embodiments, the support material or precursor thereof may have been treated, in particular in order to reduce its ability to release sodium ions, i.e. to reduce its sodium solubilization rate, or to decrease its content of water soluble silicates. A suitable treatment comprises washing with water. For example, the support material or precursor thereof may be washed in a continuous or batch fashion with hot, demineralised water, for example, until the electrical conductivity of the effluent water does not further decrease, or until in the effluent the content of sodium or silicate has become very low. A suitable temperature of the demineralised water is in the range of 80 to 100° C., for example 90° C. or 95° C. Alternatively, the support material or precursor thereof may be washed with base and subsequently with water. After washing, the support material or precursor thereof may typically be dried. Reference may be made to U.S. Pat. No. 6,368,998, which is incorporated herein by reference. Catalysts which have been prepared by using the support material or precursor material that has been so treated have an improved performance in terms of an improved initial activity, initial activity and/or selectivity stability.

The dough comprises a silver component. The silver component may be dispersed metallic silver, or alternatively the silver component may comprise a compound of cationic silver. Cationic silver may be reduced to metallic silver at any stage of the catalyst preparation, for example during the drying of the shaped particles or in a subsequent step. Reducing agents may be included in the dough, which effect reduction of cationic silver during the drying of the shaped particles. Reduction during the step of drying or during a subsequent step may advantageously be effected by using a gaseous reducing agent. The gaseous reducing agent may be, for example, hydrogen or an olefin, such as ethylene or propylene. Reduction may be effected during an initial stage of an olefin epoxidation process when the shaped catalyst is contacted with the feed comprising the olefin.

Suitable cationic silver compounds are, for example, nitrates, acetates, carbonates, citrates, oxalates, lactates of cationic silver as such or as an amine complex. Suitable complexes of amines may be based on a mono-amine, but preferably they are based on a diamine, in particular a vicinal diamine. Examples of mono-amines are 2-ethanolamine and 2-propanolamine. Examples of diamines are 1,2-ethylene diamine, 1,2-propylene diamine, 2,3-butylene diamine. A preferred cationic silver compound is a silver/1,2-ethylene diamine oxalate complex. The acetates, lactates, citrates and oxalates mentioned in this context enable at least a portion of the cationic silver to be reduced during the drying of the shaped particles. Such complexes and their conversion to metallic silver are known from U.S. Pat. No. 4,761,394, and U.S. Pat. No. 4,766,105, which are incorporated herein by reference.

The dough may comprise, as an additional component, at least one further element or compound thereof which acts as a promoter when the shaped catalyst is used as an epoxidation catalyst. Eligible further elements may be selected from the group of nitrogen, sulfur, phosphorus, boron, fluorine, Group IA metals, Group IIA metals, rhenium, molybdenum, tungsten, chromium, titanium, hafnium, zirconium, vanadium, thallium, thorium, tantalum, niobium, gallium and germanium and mixtures thereof. Preferably the Group IA metals are selected from lithium, potassium, rubidium and cesium. Most preferably the Group IA metal is lithium, potassium and/or cesium. Preferably the Group IIA metals are selected from calcium and barium. Where possible, the further element may suitably be provided as an oxyanion, for example, as a sulfate, borate, perrhenate, molybdate or nitrate, in salt or acid form.

Preferably, the further element is selected from rhenium, molybdenum, tungsten, and a Group IA metal, which may each be present in a quantity of from 0.01 to 500 mmole/kg, calculated as the element (rhenium, molybdenum, tungsten or the Group IA metal) on the shaped catalyst. More preferably, the further element is rhenium, in particular together with one or more of tungsten, molybdenum, chromium, sulfur, phosphorus, and boron, and in particular together with a Group IA metal. Compounds of nitrogen may be nitrate- or nitrite-forming compounds, which may be present in a quantity of from 0.01 to 500 mmole/kg, calculated as nitrogen on the shaped catalyst. The nitrate- or nitrite-forming compounds and particular selections of nitrate- or nitrite forming compounds are as defined hereinafter. The nitrate- or nitrite-forming compound is in particular a Group IA metal nitrate or a Group IA metal nitrite. Again, rhenium, molybdenum, tungsten or the nitrate- or nitrite-forming compound may suitably be provided as an oxyanion, for example as a perrhenate, molybdate, tungstate or nitrate, in salt or acid form.

Preferred amounts of catalytic components of the dough are, when calculated as the element, relative to the weight of the shaped catalyst:

silver from 10 to 500 g/kg, more preferably from 50 to 500 g/kg, most preferably from 50 to 400 g/kg, in particular from 50 to 250 g/kg, rhenium from 0.01 to 50 mmole/kg, if present, the rhenium co-promoter (that is a promoter comprising tungsten, molybdenum, chromium, sulfur, phosphorus, boron, as mentioned hereinbefore) each from 0.1 to 30 mmole/kg, if present, and the Group IA metal each from 0.1 to 500 mmole/kg, if present.

As used herein, the quantity of Group IA metal present in the catalyst is deemed to be the quantity in so far as it can be extracted from the shaped catalyst with de-ionized water at 100° C. The extraction method involves extracting a 10-gram sample of the shaped catalyst three times by heating it in 20 ml portions of de-ionized water for 5 minutes at 100° C. and determining in the combined extracts the relevant metals by using a known method, for example atomic absorption spectroscopy.

The dough may comprise a liquid, which will give the dough a consistency suitable for moulding it into the desired shape when using a selected moulding technique. Depending on the selected moulding technique, the quantity of liquid may be for example in the range of from 1 to 70% w, and typically in the range of from 5 to 60% w, relative to the total weight of the dough. More typically, the quantity of liquid may be in the range of from 7 to 40% w, in particular from 10 to 35% w, relative to the total weight of the dough. Suitable liquids are aqueous liquids, and non-aqueous liquids. Aqueous liquids are suitably water, or a mixture of water and an organic compound, such as, for example, methanol, ethanol, acetone, amine, formaldehyde, or a carbohydrate.

In advantageous embodiments the dough may comprise a carboxylic acid having in its molecular structure at least 2 carbon atoms and typically having at most 8 carbon atoms, in particular at most 6 carbon atoms, more in particular at most 4 carbon atoms. The carboxylic acid may or may not partly or wholly be present in the dough in ionized form, that is in carboxylate form. The carboxylic acid may comprise in its molecular structure a single carboxyl group or a plurality of carboxyl groups, or it may have hydroxy groups, typically one, two or three hydroxyl groups, in addition to one or more carboxyl groups. In particular, the carboxylic acid may comprise in its molecular structure two carboxyl groups. Examples of suitable carboxylic acids are acetic acid, lactic acid, adipic acid, citric acid, maleic acid, malonic acid and succinic acid. A preferred carboxyl acid is oxalic acid. The presence of such carboxylic acids in the dough is advantageous in that it improves the moulding of the dough into shaped particles, in particular by extrusion. The presence of such carboxylic acids also tends to improve the performance of the catalyst, typically the initial selectivity, in particular when the catalyst is operated at conditions of a relatively low gas hourly space velocity (GHSV), as defined hereinafter, for example lower than 7000 Nl/(l.h). The quantity of the carboxylic acid present in the dough may be more than 1% w, for example more than 5% w, typically at least 8% w, preferably at least 10% w, relative to the weight of the support material or precursor thereof. The quantity of the carboxylic acid present in the dough may be at most 25% w, typically at most 20% w, preferably at most 15% w, relative to the weight of the support material or precursor thereof.

In an embodiment, amongst others, a solution comprising a silver diamine complex and a reducing acid may be prepared, for example as taught in U.S. Pat. No. 4,766,105, and additional promoter components, if any, and further silver component, if any, may be added to the solution, and the mixture so obtained is mixed with the support material or a precursor thereof, to form the dough. In another embodiment, a dry mixture of the solid components of the dough, amongst which the support material or a precursor thereof, may be admixed with a solution of catalyst components, to form the dough. In a preferred embodiment, amongst others, the silver component and promoter components, if any, may be dissolved or otherwise mixed with at least a portion of the liquid and then combined with the support material or precursor thereof, to form the dough. In this preferred embodiment a catalyst can be prepared which provides an improved performance, typically in terms of the initial selectivity, in particular when the catalyst is operated at conditions of a relatively low GHSV, as defined hereinafter.

The shaped particles may be formed from the dough by any convenient moulding process, such as sieving, spraying, or spray drying, but preferably they are moulded by extrusion, agglomeration or pressing. For applicable methods, reference may be made to, for example, U.S. Pat. No. 5,145,824, U.S. Pat. No. 5,512,530, U.S. Pat. No. 5,384,302, U.S. Pat. No. 5,100,859 and U.S. Pat. No. 5,733,842, which are herein incorporated by reference.

Examples of agglomeration include, but are not limited to, tabletting, briquetting, pelleting, rolling, and tumbling. Methods of pressing include single-action pressing, double-action pressing, roll pressing, multiple pressing, isostatic pressing, hot pressing, as well as other pressing methods known to one skilled in the art. Reference may be made to *Size Enlargement by Agglomeration*, by Wolfgang Pietsch (John Wiley and Sons, 1991), pages 12-18 and 118.

To facilitate such moulding processes, in particular extrusion, the dough may suitably comprise up to about 30% w and preferably from 2 to 25% w, based on the weight of the dough, of extrusion aids. Suitable extrusion aids may be for example petroleum jelly, hydrogenated oil, synthetic alcohol, synthetic ester, glycol, polyolefin oxide, polyethylene glycol, or a saturated or unsaturated fatty acid having more than 8 carbon atoms.

The shaped particles may be dried at a temperature below 1400° C., preferably at a temperature of at most 1000° C., more preferably at most 600° C., in particular at most 550° C., more in particular at most 500° C. Typically, drying may take place at a temperature of at least 50° C., more typically at least 250° C., in particular at least 300° C. Typically drying is carried out for a period of up to 100 hours and preferably for from 5 minutes to 50 hours. Drying may be carried out in any atmosphere, such as in air, nitrogen, or helium, or mixtures thereof. Drying may also be carried out in a reducing atmosphere, enabling reduction of cationic silver as described hereinbefore. Preferably, in particular when the shaped particles contain organic material, the drying is at least in part or entirely carried out in an oxidizing atmosphere, such as for example in air or in another oxygen containing atmosphere.

In particular when the drying is performed at a temperature of at least 50° C., more typically at least 250° C., in particular at least 300° C., and at a temperature of at most 600° C., more typically at most 550° C., in particular at most 500° C., a mechanically stronger shaped catalyst is obtained, as can be found by attrition and/or crush strength tests. Also, when using the catalyst so obtained in an epoxidation process, a more rapid start-up of the epoxidation process may be accomplished, which means that the initial selectivity may be reached at a lower cumulative olefin oxide production, and substantially without detriment to other performance properties, for example initial activity, initial selectivity, activity stability and selectivity stability.

The attrition test as referred to herein is in accordance with ASTM D4058-96, wherein the test sample is tested as such after its preparation, that is with elimination of Step 6.4 of the said method, which represents a step of drying the test sample. The attrition measured for the shaped catalyst in accordance to the invention is typically at most 50% w, preferably at most 40% w, in particular at most 30% w, more in particular at most 25% w. Frequently, the attrition is at least 10% w, in particular at least 15% w.

The crush strength as referred herein is as measured in accordance with ASTM D6175-98, wherein the test sample is tested as such after its preparation, that is with elimination of Step 7.2 of the said method, which represents a step of drying the test sample. The crush strength of the shaped catalyst in accordance with the invention, in particular when measured as the crush strength of hollow cylindrical particles of 8.8 mm external diameter and 3.5 mm internal diameter, is typically at least 2 N/mm, preferably at least 4 N/mm, in particular at least 6 N/mm, and more in particular 8 N/mm. The crush strength, in particular when measured as the crush strength of hollow cylindrical particles of 8.8 mm external diameter and 3.5 mm internal diameter, is frequently at most 25 N/mm, in particular at most 20 N/mm, and more in particular at most 15 N/mm. When the shaped catalyst is present as shaped particles of a certain shape other than the particular hollow cylinders as defined, the crush strength of the shaped catalyst being present as the particular hollow cylinders is measured by repeating the preparation of the catalyst with the difference that the dough is moulded into shaped particles which are the particular hollow cylinders, instead of moulding into the shaped particles of the certain shape, and the crush strength of the hollow cylinders obtained is measured. The catalyst particles having the shape of the particular hollow cylinder have a cylindrical bore, defined by the internal diameter, which is co-axial with the external cylinder. Such catalyst particles, when they have a length of about 8 mm, are frequently referred to as "nominal 8 mm cylinders", or "standard 8 mm cylinders".

The shape and size of the shaped particles is in general determined by the needs of an epoxidation process and the dimensions of an epoxidation reactor in which they are to be deposited. Generally, it is found very convenient to use shaped particles in the form of, for example, trapezoidal bodies, cylinders, saddles, spheres, tablets, briquettes, doughnuts. The shaped particles may typically have a largest outer dimension in the range of from 3 to 15 mm, preferably from 5 to 10 mm. They may be solid or hollow, that is they may have a bore. Cylinders may be solid or hollow, and they may have a length typically from 3 to 15 mm, more typically from 5 to 10 mm, and they may have a cross-sectional, outer diameter typically from 3 to 15 mm, more typically from 5 to 10 mm. The ratio of the length to the cross-sectional diameter of the cylinders may typically be in the range of from 0.5 to 2, more typically from 0.8 to 1.25. The shaped particles, in particular the cylinders, may be hollow, having a bore typically having a diameter in the range of from 0.1 to 5 mm, preferably from 0.2 to 2 mm. The presence of a relatively small bore in the shaped particles increases their crush strength and the achievable packing density, relative to the situation where the particles have a relatively large bore. The presence of a relatively small bore in the shaped particles is beneficial in the drying of the shaped catalyst, relative to the situation where the particles are solid particles, that is having no bore.

If desired, further materials may be deposited onto the shaped catalyst, for example by impregnation or by coating, in order to further enhance its performance. However, this is normally not a preferred embodiment, as it renders the preparation of the shaped catalyst more complicated. It is preferred that all such further materials are included in the dough before it is moulded into shaped particles.

Although the epoxidation process may be carried out in many ways, it is preferred to carry it out as a gas phase process, i.e. a process in which the feed is contacted in the gas phase with the shaped catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Mixtures of olefins may be used. Typically, the olefin is a monoolefin, for example 2-butene or isobutene. Preferably, the olefin is a mono-α-olefin, for example 1-butene or propylene. The most preferred olefin is ethylene.

The olefin concentration in the feed may be selected within a wide range. Typically, the olefin concentration in the feed will be at most 80 mole %, relative to the total feed. Preferably, it will be in the range of from 0.5 to 70 mole %, in particular from 1 to 60 mole %, on the same basis. As used herein, the feed is considered to be the composition which is contacted with the shaped catalyst.

The epoxidation process may be air-based or oxygen-based, see "Kirk-Othmer Encyclopedia of Chemical Technology", $3^{rd}$ edition, Volume 9, 1980, pp. 445-447. In the air-based process air or air enriched with oxygen is employed as the source of the oxidizing agent while in the oxygen-based processes high-purity (at least 95 mole %) oxygen is employed as the source of the oxidizing agent. Presently most epoxidation plants are oxygen-based and this is a preferred embodiment of the present invention.

The oxygen concentration in the feed may be selected within a wide range. However, in practice, oxygen is generally applied at a concentration which avoids the flammable regime. Typically, the concentration of oxygen applied will be within the range of from 1 to 15 mole %, more typically from 2 to 12 mole % of the total feed.

In order to remain outside the flammable regime, the concentration of oxygen in the feed may be lowered as the concentration of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifier. Nitrogen oxides, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in low concentration in the feed, for example up to 0.1 mole %, relative to the total feed, for example from $0.01 \times 10^{-4}$ to 0.01 mole %. In particular when the olefin is ethylene, it is preferred that the reaction modifier is present in the feed at a concentration of from $0.1 \times 10^{-4}$ to $50 \times 10^{-4}$ mole %, in particular from $0.3 \times 10^{-4}$ to $30 \times 10^{-4}$ mole %, relative to the total feed.

In addition to the olefin, oxygen and the reaction modifier, the feed may contain one or more optional components, such as carbon dioxide, inert gases and saturated hydrocarbons. Carbon dioxide is a by-product in the epoxidation process. However, carbon dioxide generally has an adverse effect on the catalyst activity. Typically, a concentration of carbon dioxide in the feed in excess of 25 mole %, preferably in excess of 10 mole %, relative to the total feed, is avoided. A concentration of carbon dioxide as low as 1 mole % or lower, relative to the total feed, may be employed. Inert gases, for example nitrogen or argon, may be present in the feed in a concentration of from 30 to 90 mole %, typically from 40 to 80 mole %. Suitable saturated hydrocarbons are methane and ethane. If saturated hydrocarbons are present, they may be present in a quantity of up to 80 mole %, relative to the total feed, in particular up to 75 mole %. Frequently they are present in a quantity of at least 30 mole %, more frequently at least 40 mole %. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. Gas hourly space velocity ("GHSV") is the unit volume of gas at normal temperature and pressure (0° C., 1 atm, i.e. 101.3 kPa) passing over one unit volume of packed catalyst per hour. Preferably, when the epoxidation process is as a gas phase process involving a packed bed of the shaped catalyst particles, the GHSV may be in the range of from 1200 to 12000 Nl/(l.h), and, more preferably, GSHV is in the range of from 1500 to less than 10000 Nl/(l.h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour. As used herein, the work rate is the amount of the olefin oxide produced per unit volume of the packed bed of the shaped catalyst particles per hour and the selectivity is the molar quantity of the olefin oxide formed relative to the molar quantity of the olefin converted.

The olefin oxide produced may be recovered from the reaction mixture by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

The olefin oxide produced in the epoxidation process may be converted into a 1,2-diol, a 1,2-diol ether, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise, for example, reacting the olefin oxide with ammonia. Anhydrous or aqueous ammonia may be used, although anhydrous ammonia is typically used to favour the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the low-molecular weight organic compounds mentioned herein, for example the olefins, 1,2-diols, 1,2-diol ethers, alkanolamines and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Shaped Catalyst A comprising 17.8% w silver, 3.25 mmole rhenium/kg, 2 mmole tungsten/kg, 20 mmole lithium/kg and 780 mmole cesium/kg, based on the weight of the catalyst, was prepared as follows.

Silver oxide (120 g) was mixed with 85 g of a 1,2-ethylene diamine/water mixture (1/1 by weight). Subsequently, 12 g of oxalic acid and 45 g of citric acid was added to the silver oxide mixture. Thereafter, a solution of ammonium perrhenate, ammonium metatungstate and lithium hydroxide in 11 ml of water was added, followed by adding a solution of cesium hydroxide in water. The slurry so obtained was added to 500 g of α-alumina powder A, see Table A for detailed description, and mixed in a muller for 60 minutes to obtain a dough. 14.5 g of α-alumina powder B, see Table A for detailed description, was added to obtain a consistency of the dough which was suitable for extrusion. The dough was extruded into 6 mm solid cylinders and then dried at 50° C. overnight and subsequently the temperature was increased to 120, 250 and 400° C. The temperature was held at 400° C. for an additional 1 hour, to provide Catalyst A, in accordance with the invention. The quantities of silver oxide, ammonium perrhenate, ammonium metatungstate, cesium hydroxide and lithium hydroxide were such that the shaped catalyst had a composition as specified above. The solid cylinders had dimensions as follows: 6 mm outside diameter and 6 mm height. The resulting shaped catalyst had an attrition of 35% w.

For comparison, shaped Catalyst B comprising 20% w silver, 3.25 mmole rhenium/kg, 2 mmole tungsten/kg, 20 mmole lithium/kg and 780 mmole cesium/kg, based on the weight of the catalyst, was prepared as follows.

Silver oxide (133 g) was mixed with 82 g of a 1,2-ethylene diamine/water mixture (1/1 by weight). Subsequently, 15 g of oxalic acid and 50 g of citric acid was added to the silver oxide mixture. Thereafter, a solution of ammonium perrhenate, ammonium metatungstate and lithium hydroxide in 13 ml of water was added, followed by adding a solution of cesium hydroxide in water. The slurry so obtained was added to 500 g of α-alumina powder A, see Table A for detailed description, and mixed in a muller for 60 minutes to obtain a dough. The dough was extruded into 6 mm solid cylinders and then dried at 50° C. overnight and subsequently the temperature was increased to 120, 250 and 400° C. The temperature was held at 400° C. for an additional 1 hour, to provide Catalyst B, not in accordance with the invention. The quantities of silver oxide, ammonium perrhenate, ammonium metatungstate, cesium hydroxide and lithium hydroxide were such that the shaped catalyst had a composition as specified above. The solid cylinders had dimensions as follows: 6 mm outside diameter and 6 mm height. The resulting shaped catalyst had an attrition of 46% w.

An advantage of the present invention is that catalysts made according to this invention exhibit increased attrition resistance as compared to catalysts not made according to the invention.

The catalysts may then be used to produce ethylene oxide from ethylene and oxygen. To do this, 4 g crushed samples of Catalysts A and B (14-20 mesh, or 0.84 to 1.4 mm) are each loaded into separate 4.57 mm inside diameter stainless steel U-shaped tubes. The tubes are immersed in a molten metal bath (heat medium) and the ends are connected to a gas flow system. The inlet gas flow rates are 0.28 Nl/minute. The inlet gas pressure is 1450 kPa.

The gas mixture is passed through the catalyst beds, in a "once-through" operation, during the entire test run including the start-up, and consists of 30% v ethylene, 8% v oxygen, 5% v carbon dioxide, 57% v nitrogen and 2.0 to 6.0 ppmv ethyl chloride.

The initial reactor temperature is 180° C. and this is ramped up at a rate of 10° C. per hour to 225° C. and then is adjusted so as to achieve a constant ethylene oxide content of 3.1% v in the outlet gas stream, while the ethyl chloride concentration is adjusted from time to time as to provide and maintain an optimum selectivity of the formation of ethylene oxide. Performance data at this conversion level are usually obtained when the catalyst is on stream for a total of at least 1-2 days. The testing is continued while adjusting the temperature whenever needed so as to maintain a constant ethylene oxide content of 3.1% v in the outlet gas stream.

Shaped catalysts made in accordance with this invention can have superior performance in respect of initial activity, initial selectivity, activity stability and selectivity stability.

TABLE A

| PROPERTY | Powder A (μm) | Powder B (μm) | Resulting Mixture for Catalyst A (μm) |
|---|---|---|---|
| $d_{10}$ | 1.9 | 1.1 | 1.9 |
| $d_{50}$ | 4.9 | 2.7 | 4.8 |
| $d_{90}$ | 11.5 | 6.3 | 11.3 |
| Cumulative Volume % Less than 1 μm | 2.6 | 7.9 | 2.7 |
| Cumulative Volume % Less than 2 μm | 10.3 | 31.1 | 10.8 |
| Cumulative Volume % Less than 5 μm | 49.8 | 81.8 | 50.6 |
| Cumulative Volume % Less than 10 μm | 85 | 96.4 | 85.3 |
| Volume % of particulates with particle sizes from 2 to 5 μm | 39.5 | 50.7 | 39.8 |

What is claimed is:

1. A method of preparing a shaped catalyst for the epoxidation of an olefin, which method comprises moulding a dough into shaped particles and drying the shaped particles, wherein the dough comprises a support material, or a precursor thereof, and a silver component, and wherein the support material, or the precursor thereof, has a $d_{90}$ of at least 6 μm and of at most 12.5 μm and at least 10.5% v and at most 80% v of the support material, or the precursor thereof, has a particle size less than 2 μm.

2. The method as claimed in claim 1, wherein at least 15% v of the support material, or the precursor thereof, has a particle size less than 2 μm.

3. The method as claimed in claim 1, wherein at most 60% v of the support material, or the precursor thereof, has a particle size less than 2 μm.

4. The method as claimed in claim 1, wherein at least 50% v and at most 95% v of the support material, or the precursor thereof, has a particle size less than 5 μm.

5. The method as claimed in claim 1, wherein at least 60% v of the support material, or the precursor thereof, has a particle size less than 5 μm.

6. The method as claimed in claim 1, wherein more than 25% v of the support material, or a precursor thereof, has a particle size in the range of from 2 to 5 μm.

7. The method as claimed in claim 1, wherein the support material, or the precursor thereof, has a $d_{50}$ of at most 6.5 μm.

8. The method as claimed in claim 1, wherein the support material, or the precursor thereof, has a $d_{50}$ of at most 6 μm.

9. The method as claimed in claim 1, wherein the support material, or the precursor thereof, has a $d_{50}$ of at most 4 μm.

10. The method as claimed in claim 1, wherein the support material, or the precursor thereof, is a mixture of particulate materials comprising
one or more particulate materials having a $d_{50}$ of at most 3 μm in a quantity of at least 1% w, relative to the weight of the support material, or the precursor thereof; and
one or more particulate materials having a $d_{50}$ of more than 3 μm in a quantity of at most 99% w, relative to the weight of the support material, or the precursor thereof.

11. The method as claimed in claim 1, wherein the drying of at least a portion of the shaped particles is carried out at a temperature below 1000° C.

12. The method as claimed in claim 1, wherein the drying of at least a portion of the shaped particles is carried out at a temperature in the range of from 250 to 550° C.

13. The method as claimed in claim 1, wherein the dough further comprises more than 1% w, relative to the weight of the support material, or the precursor thereof, of a carboxylic acid having in its molecular structure at least 2 carbon atoms.

14. The method as claimed in claim 13, wherein the dough comprises the carboxylic acid in a quantity in the range of from 8 to 20% w, relative to the weight of the support material, or the precursor thereof.

15. The method as claimed in claim 1, wherein the method further comprises treating the support material, or the precursor thereof, to reduce its sodium solubilization rate or to decrease its content of water soluble silicates.

16. The method as claimed in claim 1, wherein the method further comprises washing the support material, or the precursor thereof.

17. The method as claimed in claim 1, wherein a liquid comprising the silver component is combined with the support material, or the precursor thereof, to form the dough.

18. The method as claimed in claim 1, wherein the support material is an α-alumina, or a precursor thereof.

19. The method as claimed in claim 18, wherein the α-alumina is of a platelet structure.

20. The method as claimed in claim 1, wherein the dough further comprises at least one further element selected from the group of nitrogen, sulfur, phosphorus, boron, fluorine, Group IA metals, Group IIA metals, rhenium, molybdenum, tungsten, chromium, titanium, hafnium, zirconium, vanadium, thallium, thorium, tantalum, niobium, gallium, germanium and mixtures thereof.

21. The method as claimed in claim 20, wherein the further element or compound thereof is selected from the group of rhenium, molybdenum, tungsten, Group IA metals, nitrate- or nitrite-forming compounds, and mixtures thereof.

22. A shaped catalyst for the epoxidation of an olefin which is obtainable by a method which comprises moulding a dough into shaped particles and drying the shaped particles, wherein the dough comprises a support material, or a precursor thereof, and a silver component, and wherein the support material, or the precursor thereof, has a $d_{90}$ of at least 6 μm and of at most 12.5 μm and at least 10.5% v and at most 80% v of the support material, or the precursor thereof, has a particle size less than 2 μm.

23. The shaped catalyst as claimed in claim 22, wherein the shaped catalyst has an attrition of at most 40% w.

24. The shaped catalyst as claimed in claim 22, wherein the shaped catalyst has a crush strength of at least 2 N/mm.

25. The shaped catalyst as claimed in claim 22, wherein the shaped catalyst has a crush strength of at least 2 N/mm, when measured as the crush strength of hollow cylindrical particles having an external diameter of 8.8 mm and an internal diameter of 3.5 mm.

\* \* \* \* \*